United States Patent
Albinali

(10) Patent No.: US 9,554,747 B2
(45) Date of Patent: Jan. 31, 2017

(54) POWER EFFICIENT SYSTEM AND METHOD FOR MEASURING PHYSICAL ACTIVITY IN RESOURCE CONSTRAINED DEVICES

(71) Applicant: EveryFit, Inc, Cambridge, MA (US)

(72) Inventor: Fahd Khalaf Albinali, Cambridge, MA (US)

(73) Assignee: EVERYFIT, INC., Cambridge, MA (US)

(*) Notice: Subject to any disclaimer, the term of this patent is extended or adjusted under 35 U.S.C. 154(b) by 687 days.

(21) Appl. No.: 14/010,279

(22) Filed: Aug. 26, 2013

(65) Prior Publication Data

US 2015/0057967 A1 Feb. 26, 2015

(51) Int. Cl.
*G01C 17/00* (2006.01)
*A61B 5/00* (2006.01)
*A61B 5/11* (2006.01)

(52) U.S. Cl.
CPC ............... *A61B 5/681* (2013.01); *A61B 5/1118* (2013.01); *A61B 5/002* (2013.01); *A61B 5/0022* (2013.01); *A61B 2560/0209* (2013.01); *A61B 2562/0219* (2013.01)

(58) Field of Classification Search
CPC ... A61B 2562/0219; A61B 5/002; A61B 5/11; A61B 5/1118; A61B 5/681
See application file for complete search history.

(56) References Cited

U.S. PATENT DOCUMENTS 4,956,851 A 9/1990 Wolensky et al.
5,901,191 A 5/1999 Ohno
6,462,673 B1 10/2002 Brooksby et al.
6,581,100 B1 6/2003 Durin et al.
6,771,694 B1 8/2004 Baumgartner
7,103,806 B1 9/2006 Horvitz
8,044,013 B2 10/2011 Schlingloff et al.
8,378,811 B2 2/2013 Crump et al.
9,268,384 B2 * 2/2016 Scott ..................... G06F 1/3209
2013/0030711 A1 1/2013 Korhonen
2013/0085348 A1 4/2013 Devenyi et al.

(Continued)

FOREIGN PATENT DOCUMENTS

EP 1 700 281 9/2006
EP 1 870 864 12/2007

(Continued)

OTHER PUBLICATIONS

Albinali, Fahd, et al. "Using wearable activity type detection to improve physical activity energy expenditure estimation." Proceedings of the 12th ACM international conference on Ubiquitous computing. ACM, 2010.

(Continued)

*Primary Examiner* — Elias Desta
(74) *Attorney, Agent, or Firm* — Foley & Lardner LLP; Christopher J. McKenna

(57) ABSTRACT

The systems and methods described herein relate to the power efficient measurement of physical activity with a wearable sensor. More particularly, the systems and methods described herein enable the continuous activity tracking without compromising battery life. In some implementations, the wearable sensor detects movement and enters predefined power states responsive to the type of movement detected.

21 Claims, 12 Drawing Sheets

(56) References Cited

U.S. PATENT DOCUMENTS

2014/0310549 A1\* 10/2014 Herbeck .................. G06F 1/324
                                                           713/322

FOREIGN PATENT DOCUMENTS

| EP | 1 894 175      | 3/2008  |
|----|----------------|---------|
| EP | 2 310 959      | 4/2011  |
| WO | WO-01/84848    | 11/2001 |
| WO | WO-2013/089278 | 6/2013  |

OTHER PUBLICATIONS

Alireza Vahdatpour, et al., "Accelerometer-based on-body sensor localization for health and medical monitoring applications", Pervasive Mob Comput. Dec. 2011; 7(6): 746-760.

Bodhi Priyantha, et al., "Little Rock: Enabling Energy Efficient Continuous Sensing on Mobile Phones", Pervasive Computing IEEE 10.2 (2011) pp. 12-15.

Choi L., et al., "Validation of accelerometer wear and nonwear time classification algorithm", Med Sci Sports Exerc. Feb. 2011; 43(2): 357-64.

Daito Akimura, et al., "Compressed Sensing Method for Human Activity Sensing using Mobile Phone Accelerometers" 2012, IEEE.

Edward S. Sazonov, et al., "A Sensor System for Automatic Detection of Food Intake Through Non-Invasive Monitoring of Chewing", IEEE Sens J. 2012; 12(5): 1340-1348.

Guan-Zheng Liu, et al., "Estimation of Respiration Rate from Three-Dimensional Acceleration Data Based on Body Sensor Network", Telemedicine Journal and E-Health, Nov. 2011; 17(9): 705-711.

Jeremy W., "Wear Time Validation Parameters", Jul. 11, 2012, pp. 1-2, https://help.theactigraph.com/entries/21703957.

Jonathan Lester, et al., "Are You With Me?—using accelerometers to determine if two devices are carried by the same person" (2004), The College of Information Services and Technology, pp. 1-2.

Kai Kunze, et al., "Using acceleration signatures for everyday activities for on-body device location", 2007, Embedded Systems Lab, University of Passau, pp. 1-2.

Kristina Kowalski, et al., "Direct and indirect measurement of physical activity in older adults: a systematic review of the literature", International Journal of Behavioral Nutrition and Physical Activity 2012, 9:148.

Leena Choi, et al., "Validation of Accelerometer Wear and Nonwear Time Classification Algorithm", Med Sci Sports Exerc. Feb. 2011; 43(2) 357-364.

Mamaghanian, Hossein, et al. "Compressed sensing for real-time energy-efficient ECG compression on wireless body sensor nodes." Biomedical Engineering, IEEE Transactions on 58.9 (2011): 2456-2466.

Maurice R. Puyau, et al., "Validation and Calibration of Physical Activity Monitors in Children", (2002) Obesity Research, 10: 150-157.

Priyantha, N., Dimitrios Lymberopoulos, and Jie Liu. "Eers: Energy efficient responsive sleeping on mobile phones." Proceedings of PhoneSense 2010 (2010): 1-5.

Shelley S. Tworoger, et al., "Factors associated with objective (actigraphic) and subjective sleep quality in young adult women", Journal of Psychosomatic Research, vol. 59, Issue 1, Jul. 2005.

Stone KL, et al., "Actigraphy-measured sleep characteristics and risk of falls in older women", Arch Intern Med. Sep. 8, 2008; 168(16): 1768-1775.

Wang, Yi, Bhaskar Krishnamachari, and Murali Annavaram. "Semi-Markov state estimation and policy optimization for energy efficient mobile sensing." Sensor, Mesh and Ad Hoc Communications and Networks (SECON), 2012 9th Annual IEEE Communications Society Conference on. IEEE, 2012.

Wang, Yi, et al. "A framework of energy efficient mobile sensing for automatic user state recognition." Proceedings of the 7th international conference on Mobile systems, applications, and services. ACM, 2009.

Wang, Yi, et al. "Markov-optimal sensing policy for user state estimation in mobile devices." Proceedings of the 9th ACM/IEEE International Conference on Information Processing in Sensor Networks. ACM, 2010.

Yan, Zhixian, et al. "Energy-efficient continuous activity recognition on mobile phones: an activity-adaptive approach." Wearable Computers (ISWC), 2012 16th International Symposium on. IEEE, 2012.

Yang, Sungwon, and Mario Gerla. "Energy-efficient accelerometer data transfer for human body movement studies." Sensor Networks, Ubiquitous, and Trustworthy Computing (SUTC), 2010 IEEE International Conference on. IEEE, 2010.

\* cited by examiner

POWER EFFICIENT SYSTEM AND METHOD FOR MEASURING PHYSICAL ACTIVITY IN RESOURCE CONSTRAINED DEVICES

A portion of the disclosure of this patent document contains material which is subject to copyright protection. The copyright owner has no objection to the facsimile reproduction by anyone of the patent document or the patent disclosure, as it appears in the file or records of the Patent and Trademark Office, but otherwise reserves all copyright rights whatsoever.

BACKGROUND OF THE DISCLOSURE

Wearable sensor can offer great insight into the behavior of users. Unfortunately, to accurately record and characterize activity data, the wearable sensor quickly depletes its on board batteries. The requirement to replace or recharge the batteries reduces wear compliance.

BRIEF SUMMARY OF THE DISCLOSURE

The systems and methods described herein relate to the power efficient measurement of physical activity with a wearable sensor. More particularly, the systems and methods described herein enable the continuous activity tracking without compromising battery life. In some implementations, the wearable sensor detects movement and enters predefined power states responsive to the type of movement detected.

According to one aspect of the disclosure, a method for efficiently measuring physical activity with a wearable device includes waking the wearable device from a low power state. The method also includes obtaining one or more data points of a motion signal using a motion sensor of the wearable device at a first point in time with a first frequency. The method also includes determining if the one or more data points are above a first threshold and then obtaining, for a predetermined amount of time and at a second frequency, one or more additional data points of the motion signal responsive to the one or more data points being above the first threshold.

In some implementations, the method includes obtaining only one data point from the motion signal and then determining an orientation of the wearable device responsive to the one data point. In some implementations, a second data point is obtained from the motion signal after pausing for a second predetermined amount of time.

In some implementations, determining if the one or more data points are above the first threshold includes determining if each of the first data point and the second data point are above the first threshold. Determining if the one or more data points are above the first threshold can include counting a number of data points in the one or more data points that are above the first threshold, and then determining if the number is greater than a second threshold. In some implementations, determining if the one or more data points are above the first threshold also includes determining if a consecutive subset of the one or more data points are above the first threshold.

In some implementations, the method includes determining if the absolute value of a difference between the one or more data points and a previously obtained data point is above the first threshold. In some implementations, the wearable device switches to the low power state and to sampling the motion signal at the first frequency at the end of the predetermined amount of time.

In some implementations, the method further includes comparing a subset of samples sampled at the second frequency to a second threshold, and switching to the low power state if a predetermined number of the samples in the subset of samples are not greater than the second threshold. In some implementations, the second frequency is greater than the first frequency.

According to another aspect of the disclosure, a wearable device includes a processor coupled to a motion sensor. The wearable device is configured to wake from a low power state and obtain one or more data points of a motion signal at a first point in time at a first frequency. The wearable device is also configured to determine if the one or more data points are above a first threshold, and then obtain, for a predetermined amount of time and at a second frequency, one or more additional data points of the motion signal responsive to the one or more data points being above the first threshold.

In some implementations, the processor is further configured to obtain only one data point from the motion signal and then determine an orientation of the wearable device responsive to the one data point. In some implementations, the processor is also configured to pause for a second predetermined amount of time and obtain a second data point from the motion signal. In some implementations, the processor is configured to determine if each of the first data point and the second data point are above the first threshold. In certain implementations, the processor is configured to count a number of data points in the one or more data points that are above the first threshold, and determine if the number is greater than a second threshold. In some implementations, the processor is also configured to determine if a consecutive subset of the data points within the one or more data points are above the first threshold.

In some implementations, the processor is configured to switch to the low power state and the first frequency at the end of the predetermined amount of time. In some implementations, the processor configured to compare a subset of samples sampled at the second frequency to a second threshold. The processor is also configured to switch to the low power state if a predetermined number of the samples in the subset of samples are not greater than the second threshold. In certain implementations, the second frequency is greater than the first sampling frequency.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following descriptions of the sections of the specification and their respective contents may be helpful:

For purposes of reading the description of the various embodiments below, the following descriptions of the sections of the specification and their respective contents may be helpful:

Section A describes a wearable sensor.

Section B describes a network environment and computing environment which may be useful for practicing embodiments described herein.

Section C describes an embodiment of a housing for a wearable sensor.

Section D describes embodiments of systems and methods measuring physical activity with a wearable sensor in a power efficient manner.

A. Wearable Sensor Device

Prior to discussing specific embodiments of the present solution, it may be helpful to describe aspects of the device, operating environment, and associated system components (e.g., hardware elements) in connection with the methods and systems described herein.

Wearable sensor devices may be used to track physical activity, medical conditions, behavioral conditions, or be used as medical alert devices. In a clinical setting, wear compliance (i.e., the wearing of the sensor device by the patient when prescribed) is difficult to assess. Accurately detecting when a wearable sensor is worn by a user enables the correct and accurate measurement of activity and conditions by the sensing device.

Figure 1A:
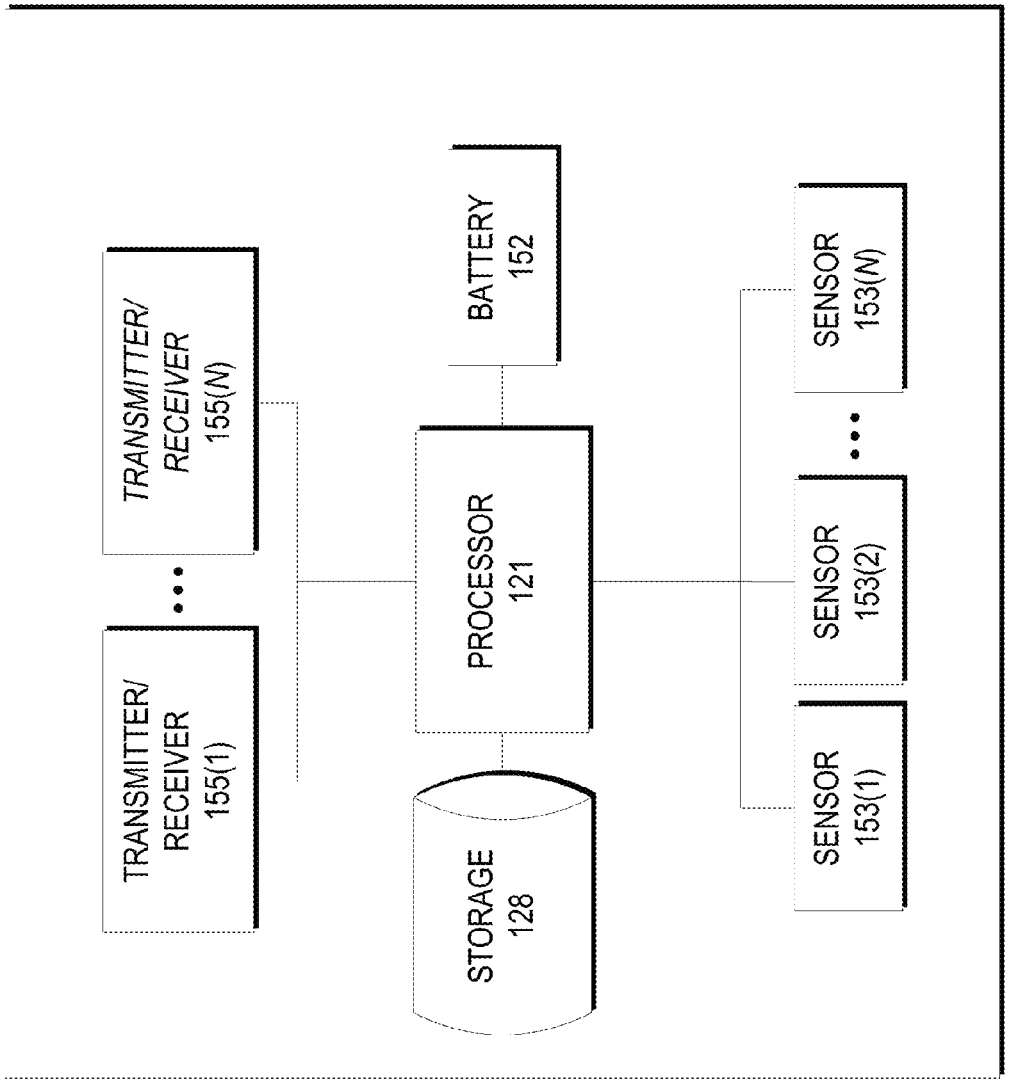
FIG. 1A is a block diagram of an embodiment of a wearable sensor.

FIG. 1A illustrates a block diagram of an embodiment of a wearable sensor 150. As described below, the outward form (i.e., housing) of the wearable sensor 150 can include many shapes, and in general may be reversibly coupled to a wearer. Internally, the wearable sensor 150 includes a processor (also referred to as a CPU) 121, which is powered by a battery 152. Also, the wearable sensor 150 can include a plurality of sensors 153(1)-153(N) (collectively referred to as sensors 153). The wearable sensor 150 can monitor behavioral and/or environmental conditions and store data into the storage device 128. The wearable sensor 150 can communicate with other devices through a data transmitter and receiver 155 module (also referred to as a TX/RX module 155).

Figure 1B:
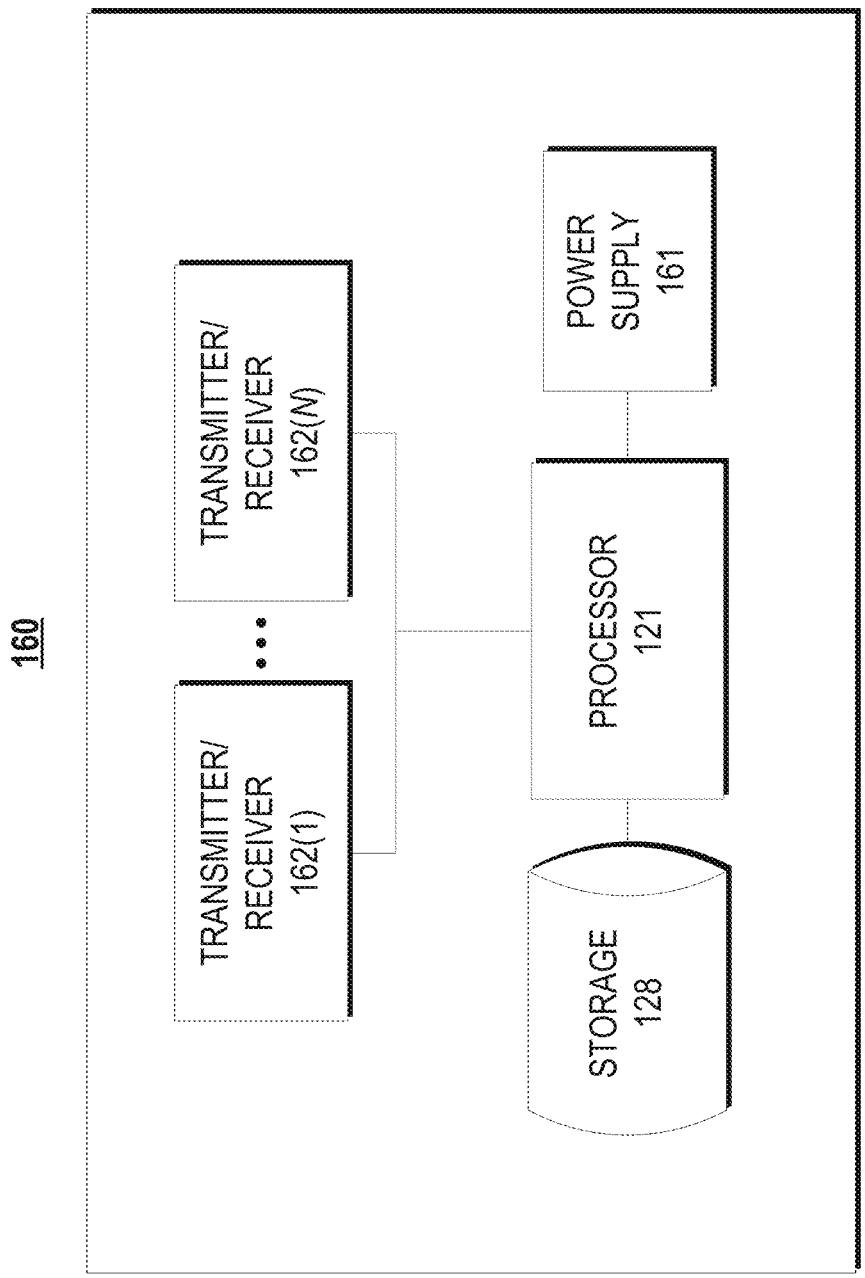
FIG. 1B is a block diagram of an embodiment of a base station.
Figure 1C:
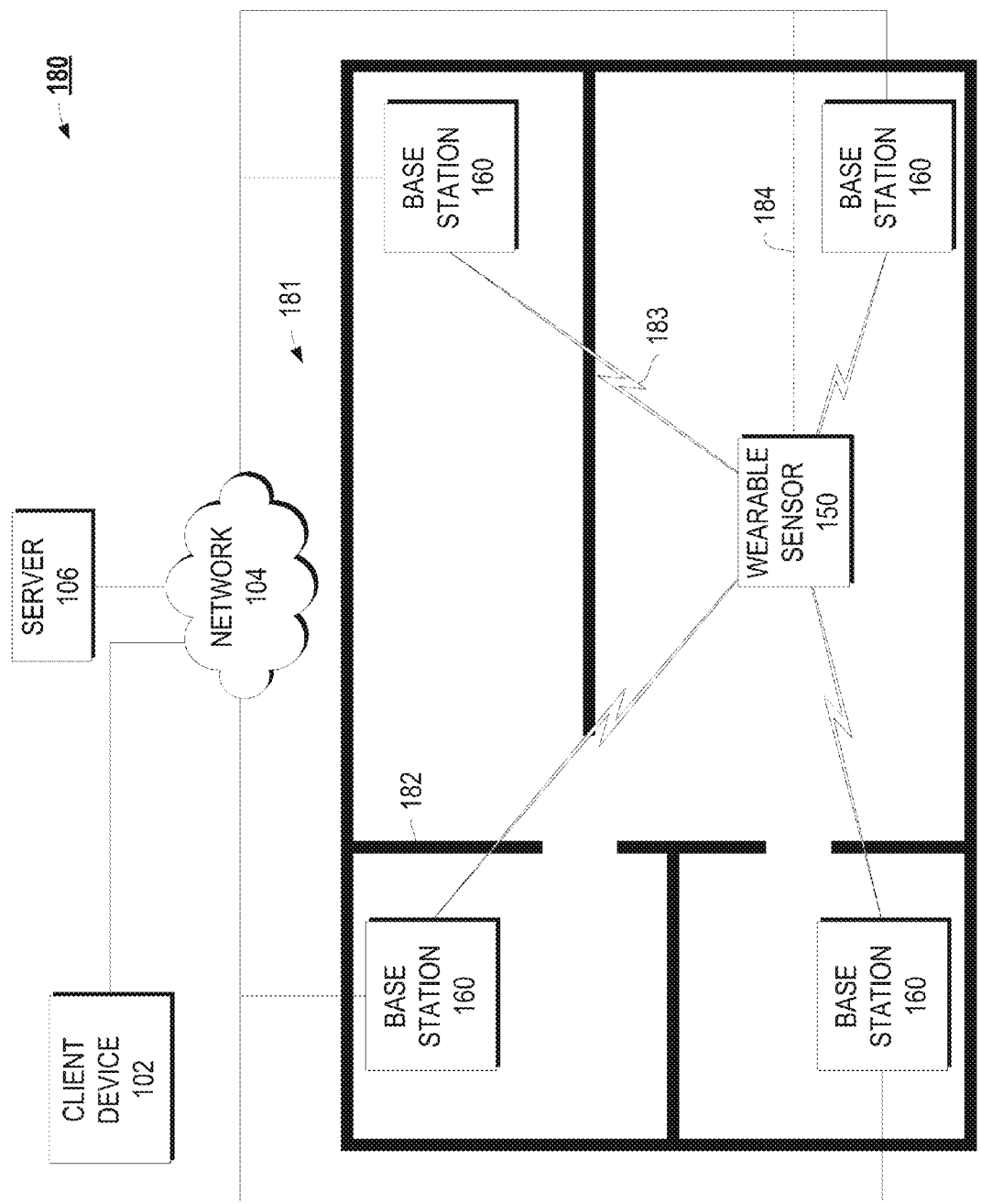
FIG. 1C is a schematic of an environment including the wearable sensor of FIG. 1A and base station of FIG. 1B.
Figure 1D:
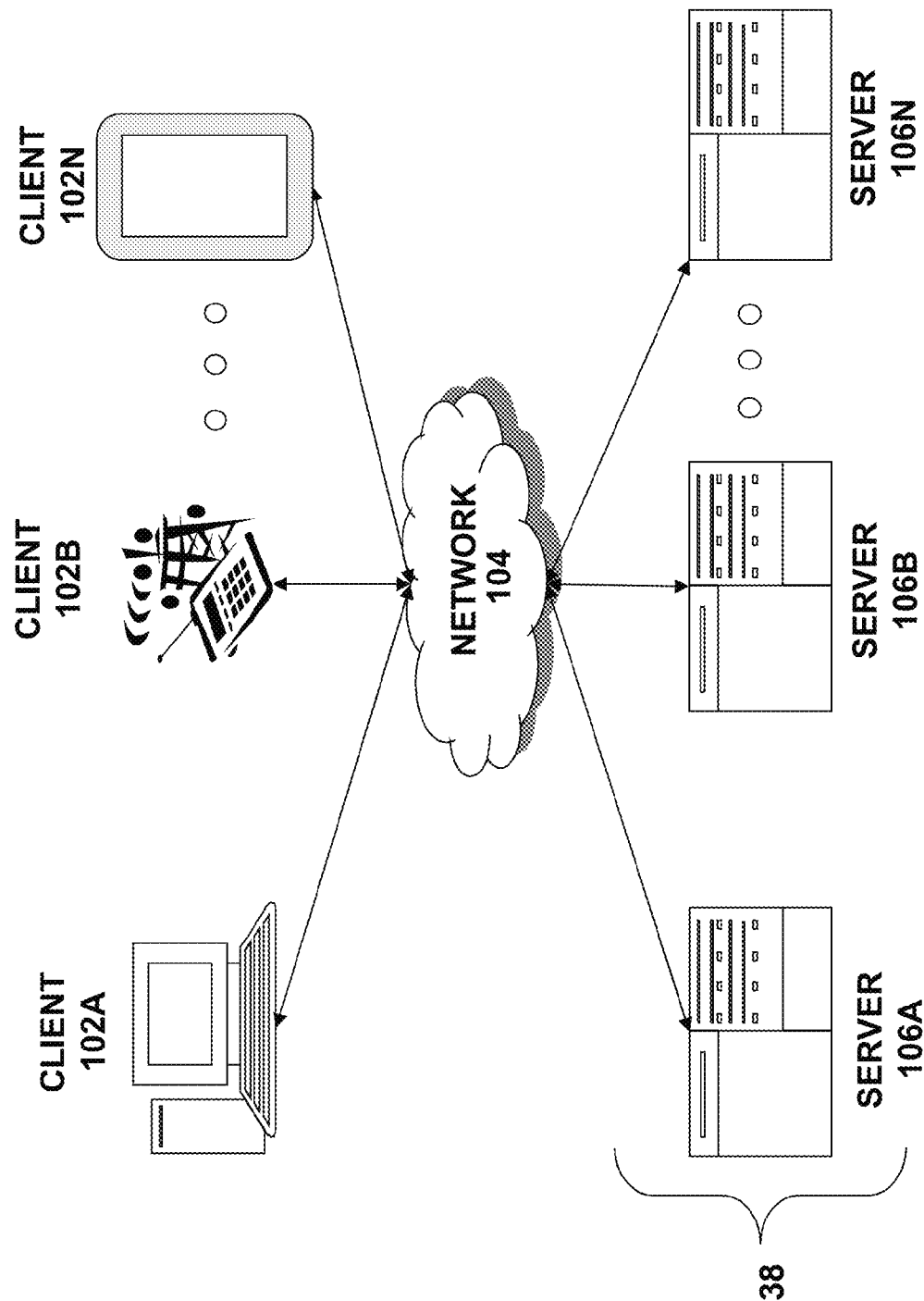
FIG. 1D is a block diagram depicting an embodiment of a network environment comprising client device in communication with server device.
Figure 1E:
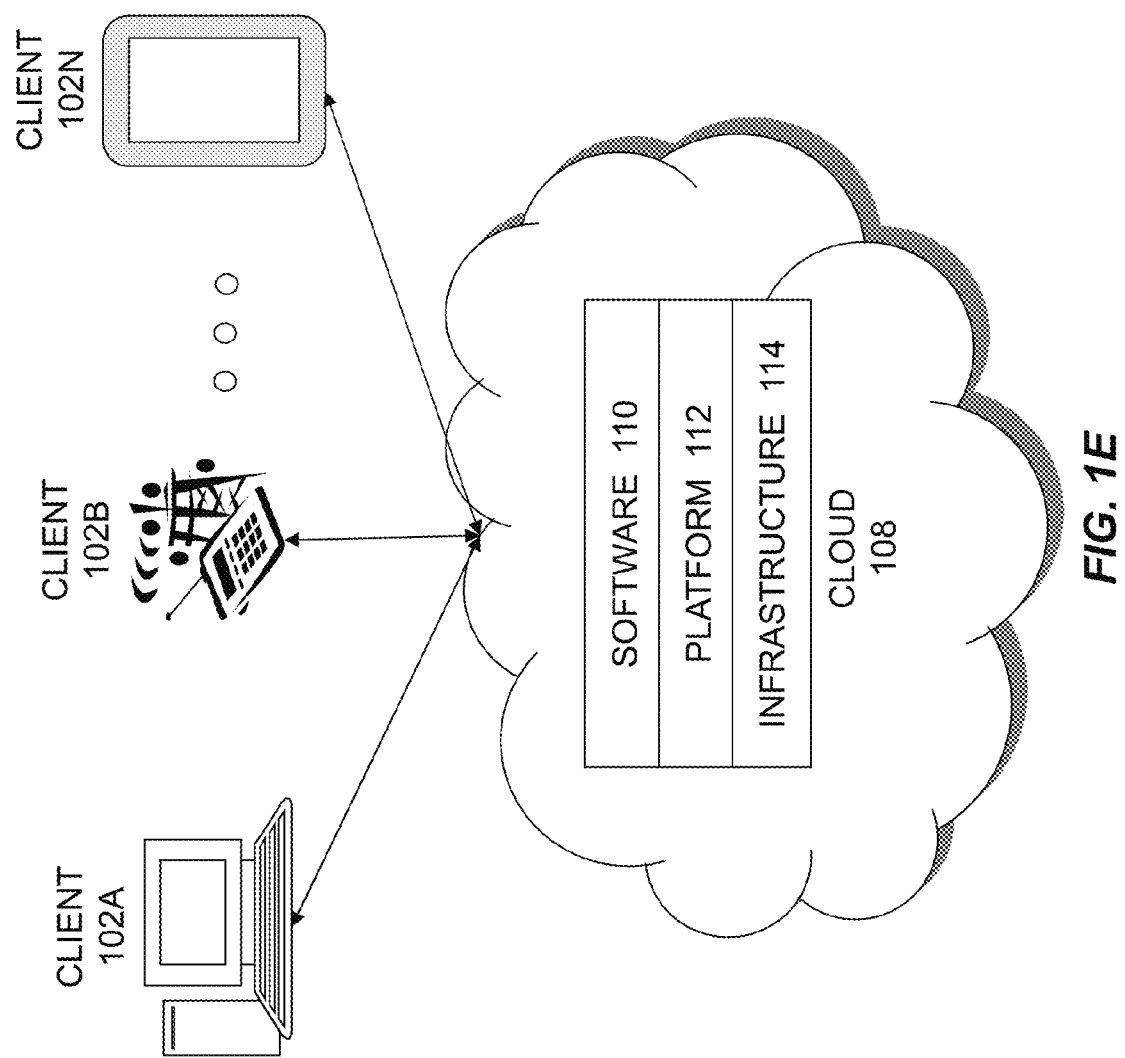
FIG. 1E is a block diagram depicting a cloud computing environment comprising client device in communication with cloud service providers.
Figure 1F:
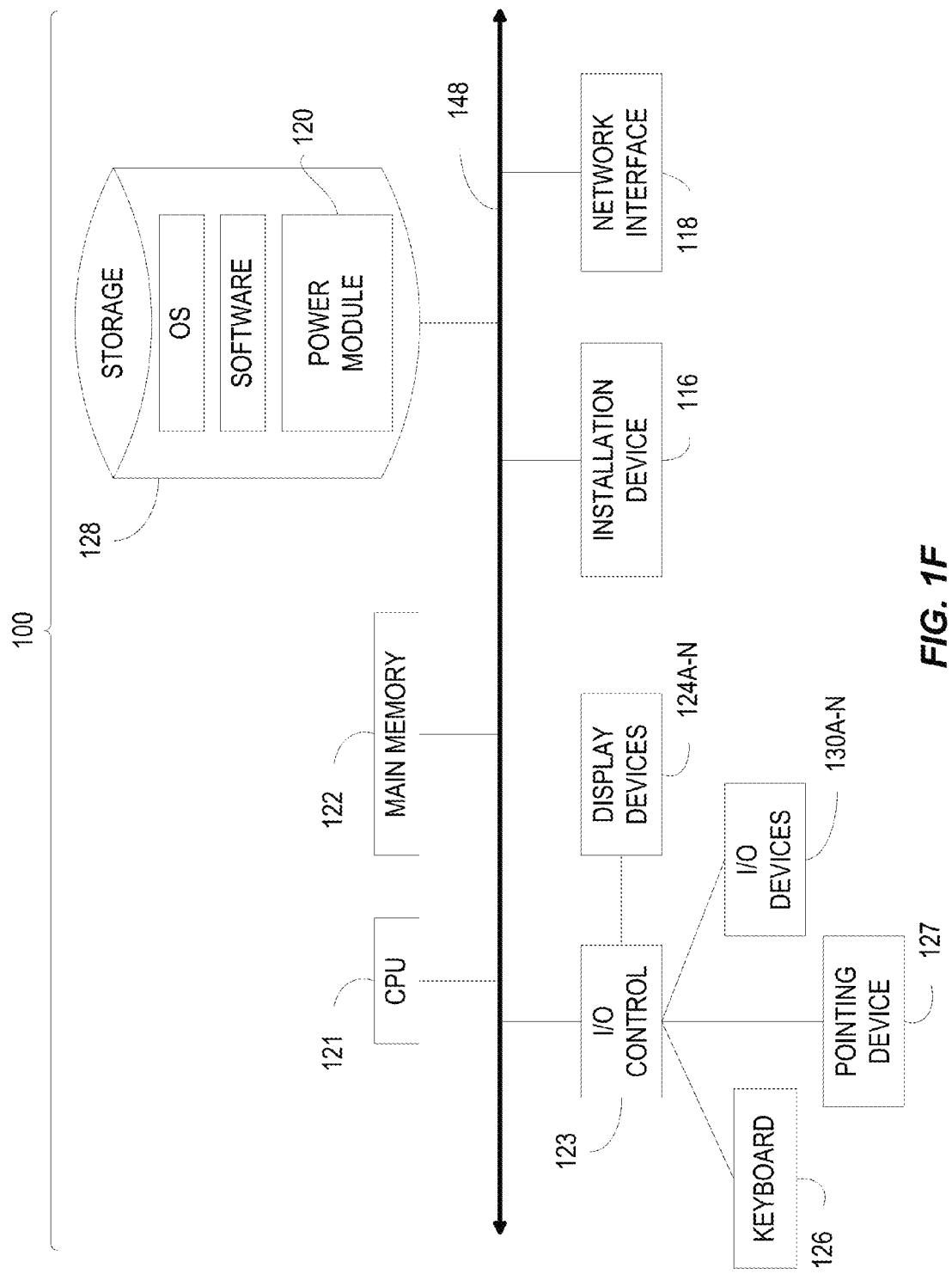
FIGS. 1F and 1G are block diagrams depicting embodiments of computing devices useful in connection with the methods and systems described herein.

The processor 121 and storage device 128 are discussed further in relation to FIGS. 1E and 1F, but in general the processor 121 is a microcontroller or central processing unit capable of executing the instructions and methods described herein. The processor 121 can include one or more analog to digital converters (A/D converters). The A/D converters may be used by the processor 121 to sample and record data from the plurality of sensors 153. In some implementations, the sensor 153 generates a digital signal, which the processor 121 can input without analog to digital conversion. Similarly, the storage device 128 may be any storage device capable of storing the instructions executed by the processor 121. In some implementations, the storage device 128 is a component of the processor 128.

In some embodiments, the storage device 128 is configured to store data obtained via the sensors 153 and/or calculations made by the processor 121. In some implementations, the storage device 128 is a stand-alone component. For example, the storage device 128 can be removeably coupled to the wearable sensor or it may be permanently coupled to the wearable sensor. For example, the storage device 128 may include a Secure Digital (SD) or other removable non-volatile memory card. In some implementations, the storage device 128 is a component of the processor 121. For example, the storage device 128 can be flash memory within the processor 121.

The wearable sensor 150 may store data in the storage device 128 prior to transmitting the data to a second device. For example, the wearable sensor 150 may transmit data to the second device at predetermined intervals (e.g., once every hour or day). In another example, the wearable sensor 150 may store data until the second device is in range, such that the data may be transferred to the second device. For example, the second device may be a base station located within the user's home. When the user (and wearable sensor 150) is away from their home, the wearable sensor 150 may store the data collected during that time onto the storage device 128. When the user arrives home the wearable sensor 150 may detect the base station and transmit the data to the base station. In some implementations, the storage device 128 is a circular storage device (e.g., a circular buffer), such that old data is automatically overwritten once the storage device 128 is full. For example, the storage device 128 may maintain the most recent day, week, or month's worth of data. In some implementations, the data stored in the buffer is divided into a plurality of subsections (e.g., newest, recent, and old data). The wearable sensor 150 may transmit one or more of the subsections to the base station responsive to a policy. For example, the wearable sensor 150 may automatically re-transmit older data stored in the circular buffer when sending new data to ensure that the old data was properly received at the base station.

The wearable sensor 150 also includes TX/RX module 155. As described below, the TX/RX module 155 enables the wearable sensor 150 to communicate with other devices. The other devices can include other wearable sensors 150, base stations, mobile phones, computers, servers, or any combination thereof. In some implementations, the wearable sensor 150 includes a plurality of TX/RX modules 155. For example, the wearable sensor 150 may include a WiFi radio and a Bluetooth radio for wireless communication and also include a universal serial bus (USB) for wired connections to other devices. In some implementations, the TX/RX modules 155 may use IEEE 802.11, Zigbee, USB, Bluetooth, Bluetooth low energy (e.g., v4), TCP/IP, sub-1 GHz (e.g. 315 MHz 433 Mhz 900 MHz) protocols such as SimpliciTI, or any combination thereof to communicate with other devices. One of ordinary skill in the art will recognize that other wired and/or wireless communication protocols may be used in the methods and systems described herein. In some implementations, the TX/RX module 155 is a component of the processor 121.

Power is supplied to the wearable sensor 150 by a battery 152 (or similar power storage device). In some implementations, the battery 152 is coupled to an energy harvester that collects environmental energy (e.g., a solar cell on the face of the wearable sensor 150). The battery 152 can supply between about 1.5 V and 9 V to the processor 121 and/or other components of the wearable sensor 150. In some implementations, the battery 152 lasts about 1-3, 2-5, 4-10, or 7-14 days before needing replacement or recharging. In other implementations, the battery 152 can last 2-6 months, 3-9 months, 8-12 months, or 1-3 years without replacement or recharging. In some implementations, the battery 152 may be a rechargeable battery. In some implementations, the rechargeable battery is charged through the above described USB port that may also be used for wired communication. The battery may be a disposable battery (e.g., a coincell battery). In some implementations, the wearable sensor 150 includes a plurality of batteries 152. The plurality of batteries 152 may be used to extend the time between battery replacement/recharging. In other implementations, one of the plurality of batteries 152 may act as a backup. For example, the backup battery may power the device in the event that the main battery 152 loses power. Similarly, the backup battery may power the wearable sensor 150 during periods of time when the main battery 152 is being replaced.

As illustrated in FIG. 1A, the wearable sensor 150 includes at least one sensor 153. The sensors 153 may be used to monitor and record a plurality of environmental parameters, physical activity parameters, behavioral parameters and medical parameters. For example, the sensors 153 enable the processor 151 to monitor factors such as temperature, light conditions, humidity, skin capacitance, skin resistance, UV light, air quality, ultrasound, FM/AM signal strength, heart rate, pulse oximetry, blood pressure, magnetometer, gas composition, pressure, altitude, breathing rate, force, location, proximity, or any combination thereof. In some implementations, the sensor 153 is a camera. The sensors 153 may measure physical activity parameters such as orientation, acceleration, position (relative or exact), number of steps taken over a period of time, overall activity level, impact (or shock) levels or any combination thereof.

The sensors 153 can include one or more of an accelerometer, gyroscope, passive vibration sensor, light sensor, temperature sensor, altitude sensor, and galvanic response sensor, GPS receiver, auditory sensors (i.e., microphone). The sensors 153 may be internal and/or external to the wearable sensor 150. For example, an accelerometer may be housed within the wearable sensor 150, while a light sensor may be disposed at least partially on the surface of the wearable sensor 150 such that it may detect the ambient lighting conditions. The processor 121 may sample the signal created by the sensors 153 at a plurality of sampling frequencies. For example, the processor 121 may sample the sensors 153 at about 0.25 Hz-5 Hz, 5 Hz-25 Hz, 25 Hz-50 Hz, 50 Hz-100 Hz, or greater than 100 Hz. In embodiments with a plurality of sensors 153, each of the sensors 153 may be sampled at a different frequency.

FIG. 1B illustrates an exemplary schematic of a base station 160 that may be used with the wearable sensor 150. The base station 160 may be a custom built device, general computing device and/or mobile phone. For example, the base station 160 may be any one of the below described client devices 102. As illustrated, the base station 160 may include one or more processors 121 and storage devices 128. The base station 160 also includes a power supply 161 and transmitters and receivers modules 162(1)-162(N) (collectively referred to as TX/RX modules 162). The power supply 161 can power the base station 160 through battery power and/or alternating current power. In some implementations, the base station 160 may include sensors similar to the above described sensors 153 of the wearable sensor 150.

The TX/RX modules 162 may be the similar to the TX/RX modules 155 in the wearable sensor 150. The TX/RX modules 162 may be configured to include a built-in network adapter, network interface card, PCMCIA network card, EXPRESSCARD network card, card bus network adapter, wireless network adapter, USB network adapter, modem or any other device suitable to communicating with devices and/or networks described herein. In some implementations, the base station 160 may include a first TX/RX module 162 that communicates with one or more wearable sensors 150 and a second TX/RX module 162 that communicates with a network.

FIG. 1C illustrates an environment 180 in which the wearable sensor 150 and base station 160 may be used. The environment 180 includes a structure 181 (e.g., a house), which includes a plurality of walls 182. As illustrated, each room of the structure 181 includes a base station 160. One of ordinary skill in the art will recognize that more than, or less than, four base stations 160 may be used with a base station 160. For example, a base station 160 may be configured to transmit a wireless signal that is detectable throughout substantially an entire house or structure. In other implementations, a wearable sensor 150 may be used without a base station 160.

The base stations 160 are in communication with a network 104. The connection may be wired or wireless. In some implementations, the communication between any two devices (e.g. a wearable sensor 150 and base station 160) in the environment 180 is encrypted. The environment 180 also includes at least one client device 102 and a server 106 are also connected to the network 104. The network 104 is described in greater detail below, but in general, the network 104 can include WANs, LANs, wired telephone networks, wireless telephone networks, or any combination thereof.

As illustrated, the wearable sensor 150 is in wireless communication with each of the base stations 160. In some implementations, the wearable sensor 150 may detect the signal 183 from each of the base stations 160, but only transmit data to a subset of the base stations 160 at any given time. In some implementations, the wearable sensor 150 and/or base stations 160 can determine the relative strength of the wireless connection between the wearable sensor 150 and base station 160. Using the relative strengths of the wireless connections, the relative position of the wearable sensor 150 can be determined. In some implementations, the relative strengths of the wireless connection is determined responsive to a received signal strength indication (RSSI) or a link quality indication (LQI). In some implementations, the relative position of the wearable sensor 150 can be determined using 1, 2, 3, 4, 5, or more base stations 160. For example, a user may have a first base station 160 located in their bedroom and a second base station 160 located in their living room. When the user and wearable sensor 150 are in the user's bedroom, the first base station 160 may have a relatively stronger connection to the wearable sensor 150 when compared to the second base station 160. Responsive to the relative connection strengths between the wearable sensor 150 and first base station 160 and wearable sensor 150 and the second base station 160 it can be determined that the user and wearable sensor 200 are located in the user's bedroom. In some implementations, a distribution of the RSSI and LQI within the environment 180 can be modeled. Applying, the wearable sensor's current wireless connection strength, the location of the wearable sensor 150 can be predicted using, for example, a particle filter.

The plurality of devices within the environment 180 are connected through the network 104. In some implementations, the wearable sensor 150 is connected to the network 104 through one or more base stations 160 via a wireless connection 183. In other implementations, the wearable sensor 150 is connected directly to the network 104 through connection 184. In yet other implementations, the wearable sensor 150 docks (or establishes a wired connection) with a base station 160 to connect to the network 104. For example, the base station 160 may collect data throughout the day. After data has been collected the user may transmit the collected data to the server 106 by connecting the wearable sensor 150 to a base station 160.

The wearable sensor 150 may communicate with other devices in the environment 180 to transmit data collected via the sensors 153. The wearable sensor 150 may establish a connection with one or more of the devices in the environment 180 at predetermined intervals (e.g., hourly, daily, weekly, or monthly), when the amount of data stored on its storage device 128 reaches a predetermined threshold, and/or the wearable sensor 150 may be in constant communication with the one or more devices when they are in range to enable wireless communication.

The environment 180 also includes a client device 102. Each of the client device 102, network 104, and server 106 are described in greater detail in relation to FIGS. 1E-1G. In brief, the client device 102 may include smart phones or other mobile devices. In some implementations, the client device 102 can also act as a base station 160. For example, the wearable sensor 150 may connect to the client device 102 via a Bluetooth connection to deliver data to the client device 102. The client device 102 may then establish a connection with the server 106 to deliver the data to the server 106. In some implementations, the client device 102 is in the possession of the user of the wearable sensor 150 and, in other implementations, the client device 102 is in the possession of a person other than the user of the wearable sensor 150. The environment 180 may include a plurality of client devices 102 that each correspond to a single wearable sensor 150. For example, a first client device 102 may be owned by the user of the wearable sensor 150 and a second client device 102 may be owned by a care taker of the user. Notifications or data corresponding to the wearable sensor 150 may be viewed by both the user and the care taker via their respective client devices 102.

In some implementations, the client device 102 may be used as an interface to the wearable sensor 150. The client device 102 may execute an application that enables a user to interact with the wearable sensor 150. The interaction may include turning the wearable sensor 150 on or off, marking events, viewing data, enabling features, or any combination thereof. In some implementations, a user can use the application to share and view data from (or with) loved-ones. Caretakers or medical professionals may use the application to view data from a patient. The application may also be used to transmit medical alters responsive to their detection by the wearable sensor 150. For example, the wearable sensor 150 may obtain motion data via a sensor 153 and transmit the data to the server 106. The user may view the trend of the motion data via the user's client device 102. In some implementations, alerts, updates, or data from an associated wearable sensor 150 is pushed to the client device 102. For example, the wearable sensor 150 may be configured to detect if the wearable sensor 150 is not being worn. If the wearable sensor 150 determines that it is not being worn, an alert may be sent to the client device 102 of a caretaker.

One of ordinary skill in the art will recognize that the methods described herein may occur on the wearable sensor 150, base station 160, client device 102, server 106, or any combination thereof. For example, the wearable sensor 150 may record motion data and transmit the data to the server 106. The server 106 may process the data to determine the wear state of the wearable sensor 150.

B. Computing and Network Environment

Prior to discussing specific embodiments of the present solution, it may be helpful to describe aspects of the operating environment as well as associated system components (e.g., hardware elements) in connection with the methods and systems described herein. Referring to FIG. 1E, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1E shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, public switching telephone network, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Wash.), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, Calif.; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store. In some embodiments, one or more servers 106 may process a distributed data set. The distributed data set may be distributed over one or more servers 106 or storage systems. In these embodiments, the servers 106 may use MapReduce or Hadoop to process the data.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Referring to FIG. 1F, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Wash., RACKSPACE CLOUD provided by Rackspace US, Inc., of San Antonio, Tex., Google Compute Engine provided by Google Inc. of Mountain View, Calif., or RIGHTSCALE provided by RightScale, Inc., of Santa Barbara, Calif. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Wash., Google App Engine provided by Google Inc., and HEROKU provided by Heroku, Inc. of San Francisco, Calif. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, Calif., or OFFICE 365 provided by Microsoft Corporation. Examples of SaaS may also include data storage providers, e.g. DROPBOX provided by Dropbox, Inc. of San Francisco, Calif., Microsoft SKYDRIVE provided by Microsoft Corporation, Google Drive provided by Google Inc., or Apple ICLOUD provided by Apple Inc. of Cupertino, Calif.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, Calif.). Clients 102 may also access SaaS resources through smartphone or tablet applications, including, e.g., Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1G:
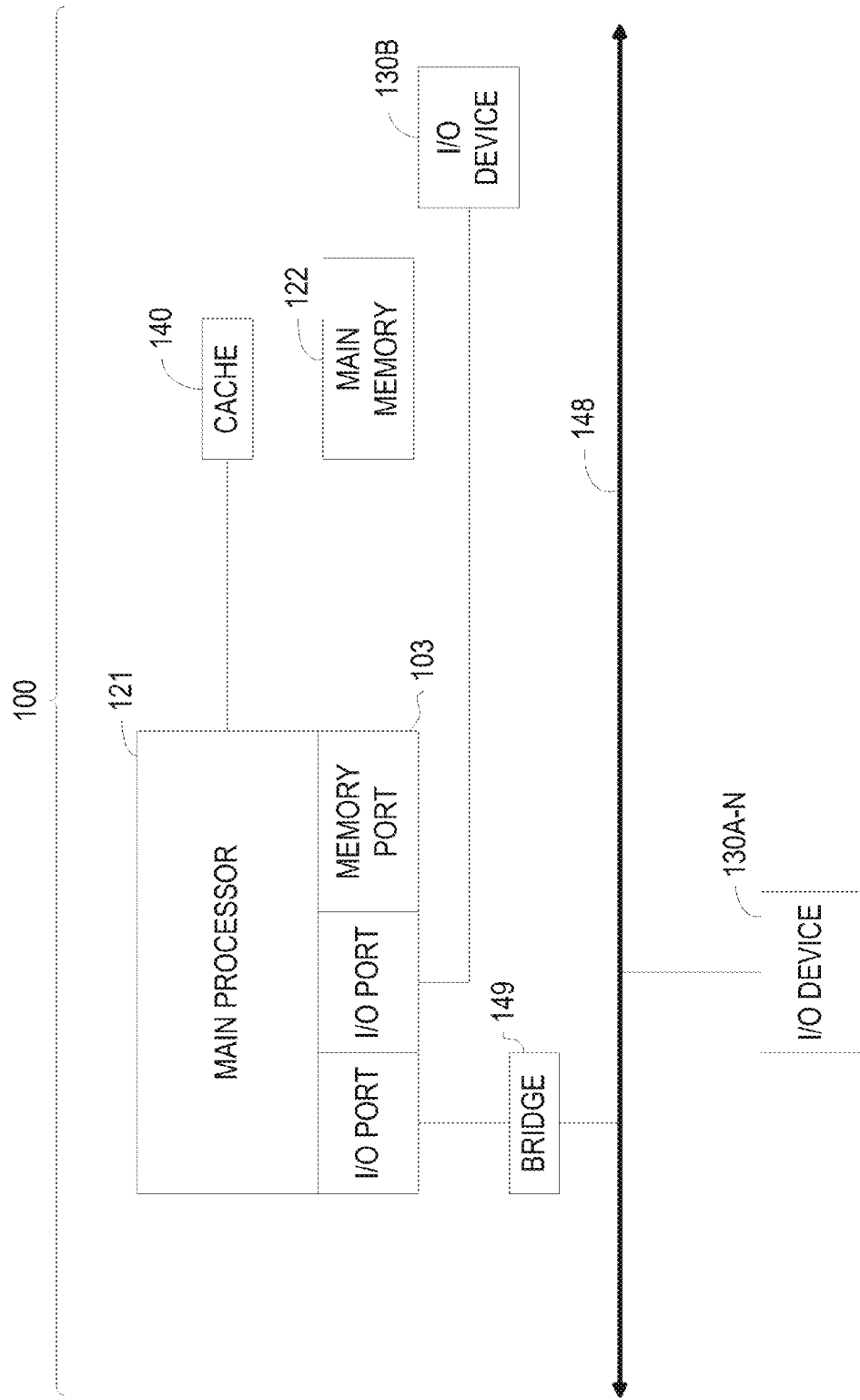

The client 102 and server 106 may be deployed as and/or executed on any type and form of computing device, e.g. a computer, network device or appliance capable of communicating on any type and form of network and performing the operations described herein. FIGS. 1G and 1D depict block diagrams of a computing device 100 useful for practicing an embodiment of the client 102 or a server 106. As shown in FIGS. 1G and 1D, each computing device 100 includes a central processing unit 121, and a main memory unit 122. As shown in FIG. 1G, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a wear detection module 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, Calif.; those manufactured by Motorola Corporation of Schaumburg, Ill.; the ARM processor and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (REDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1G, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touch-screen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1G. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1G, the computing device 100 may comprise a storage device 128 (e.g. one or more hard disk drives or redundant arrays of independent disks) for storing an operating system or other related software, and for storing application software programs such as any program related to the software 120 for the experiment tracker system. Examples of storage device 128 include, e.g., hard disk drive (HDD); optical drive including CD drive, DVD drive, or BLU-RAY drive; solid-state drive (SSD); USB flash drive; or any other device suitable for storing data.

Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as a installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11E/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Fla. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1F and 1G may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, Calif., among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Wash.

In some embodiments, the computing device 100 is a digital audio player such as the Apple IPOD, IPOD Touch, and IPOD NANO lines of devices, manufactured by Apple Computer of Cupertino, Calif. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Wash. In other embodiments, the computing device 100 is a eBook reader, e.g. the KINDLE family of devices by Amazon.com, or NOOK family of devices by Barnes & Noble, Inc. of New York City, N.Y.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

C. Wearable Sensor Housing

Figure 2A:
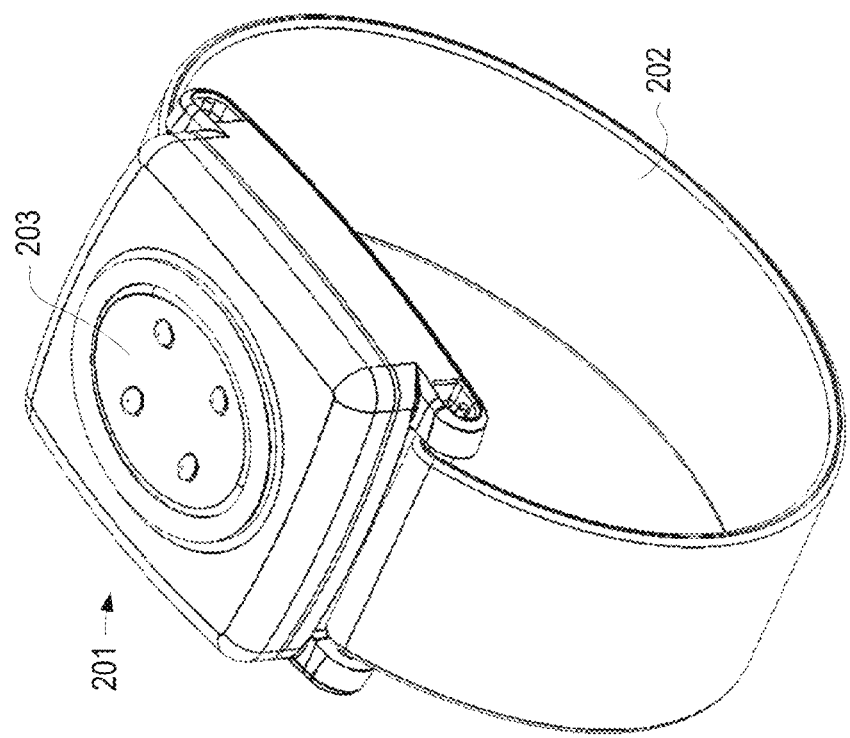
FIGS. 2A and 2B illustrate solid models of a wearable sensor.
Figure 2B:
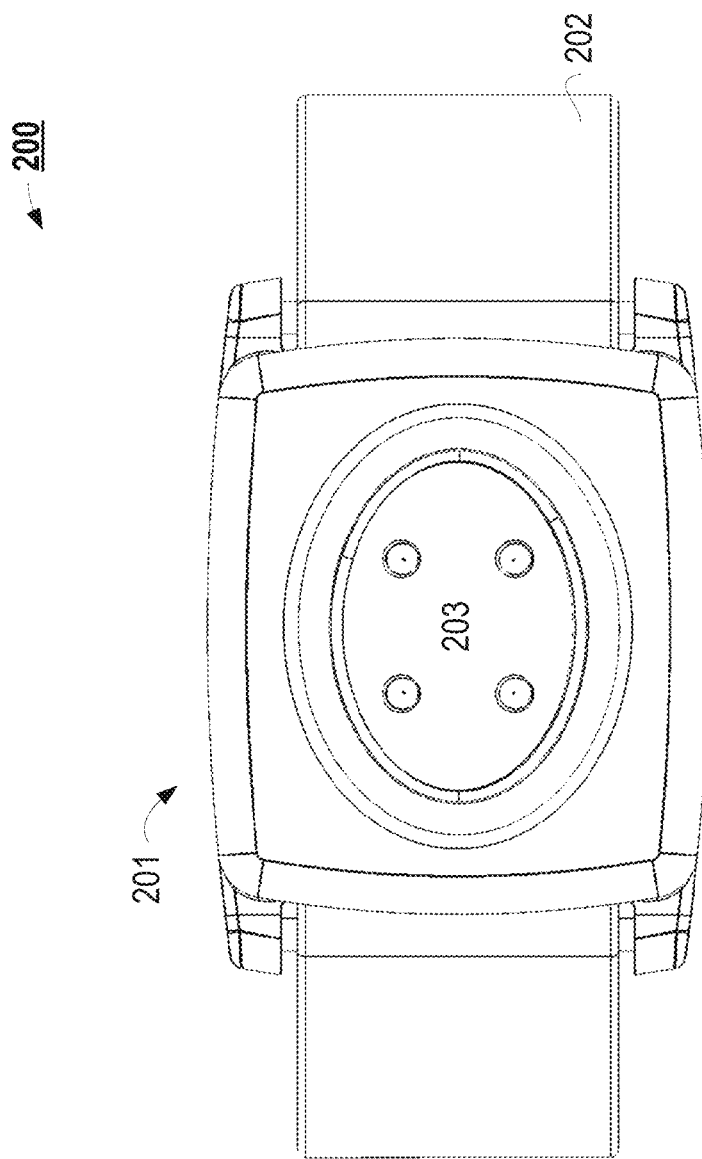

FIGS. 2A and 2B illustrate isometric and top views, respectively, of an exemplary wearable sensor 200. The wearable sensor 200 includes a housing 201, which is coupled to a user with a strap 202. In some implementations, a user may wear the wearable sensor 200 like a wrist watch. In other implementations, the wearable sensor 200 may include a clip, pin, or similar means to couple the wearable sensor 200 to a user. In some implementations, the wearable sensor 200 is incorporated into a watch or piece of jewelry (e.g., a bracelet or necklace).

The housing 201 houses the components described above in relation to FIG. 1A. The above described sensors 153 may be internal and/or external to the housing 201. For example, the wearable sensor 200 may include an accelerometer, which need not be exposed to the outside environment. In another example, the wearable sensor 200 may include an ambient light sensor that is exposed to the outside environment such that it can measure the light levels. Similarly, the wearable sensor 200 may include a galvanic response sensor on the bottom surface of the housing 201. The galvanic sensor may make contact with a user's skin and be configured to determine when it is in contact with a user's skin and when it is not in contact with a user's skin.

As illustrated, the wearable sensor 200 includes a button 203. In some implementations, the wearable sensor 200 includes a plurality of buttons and/or a screen. In some implementations, the screen is a touch screen. A user may use the bottom 203 to mark events. For example, a user may mark the beginning of physical activity. In some implementations, the button 203 is coupled to an input on the above described processor 121. When the button 203 is depressed, the processor 121 may mark the event. For example, the processor 121 may store a time stamp of when the button 123 was depressed in the storage device 128.

In some implementations, the wearable sensor 200 includes medical alert functionality. The button 203 may be used to request help or to send an alert that a medical incident is occurring. For example, if the user falls the user may press the button 203 and the wearable sensor 200 may send an alert to the client device 102 of a care taker.

In some implementations, the functionality of a button 203 and/or screen located on the wearable sensor 200 is achieved through a client device 102. For example, a user's smart phone may run an application that corresponds to the wearable sensor 200. The application may be in communication with the wearable sensor 200 through a data connection on the phone and wearable sensor 200. The application may provide the user with information relevant to the wearable sensor 200. In some implementations, the application may enable the user to activate features on the wearable sensor 200 as if the user was depressing a physical button on the wearable sensor 200. For example, the wearable sensor 200 may include an "activity button," that when activated causes the wearable sensor 200 to mark a time stamp indicating when the activity button was depressed in the application.

The wearable sensor may be designed and constructed to have a predetermined shape or form that provides a predetermined orientation when the wearable sensor is lying at rest, falls and lies at rest or is placed down by the wearer on a surface. In some implementations, the wearable sensor 200 is configured such that when not worn, it defaults to a particular orientation. For example, the top of the housing 201 may be dome shaped and weighted to one side. When not worn the wearable sensor 200 may lean to the weighted side (also referred to as the wearable sensor's default orientation). When the wearable sensor 200 (or other device in the environment 180) detects the default orientation, the wearable sensor 200 may determine that it is not being worn.

Figure 2C:
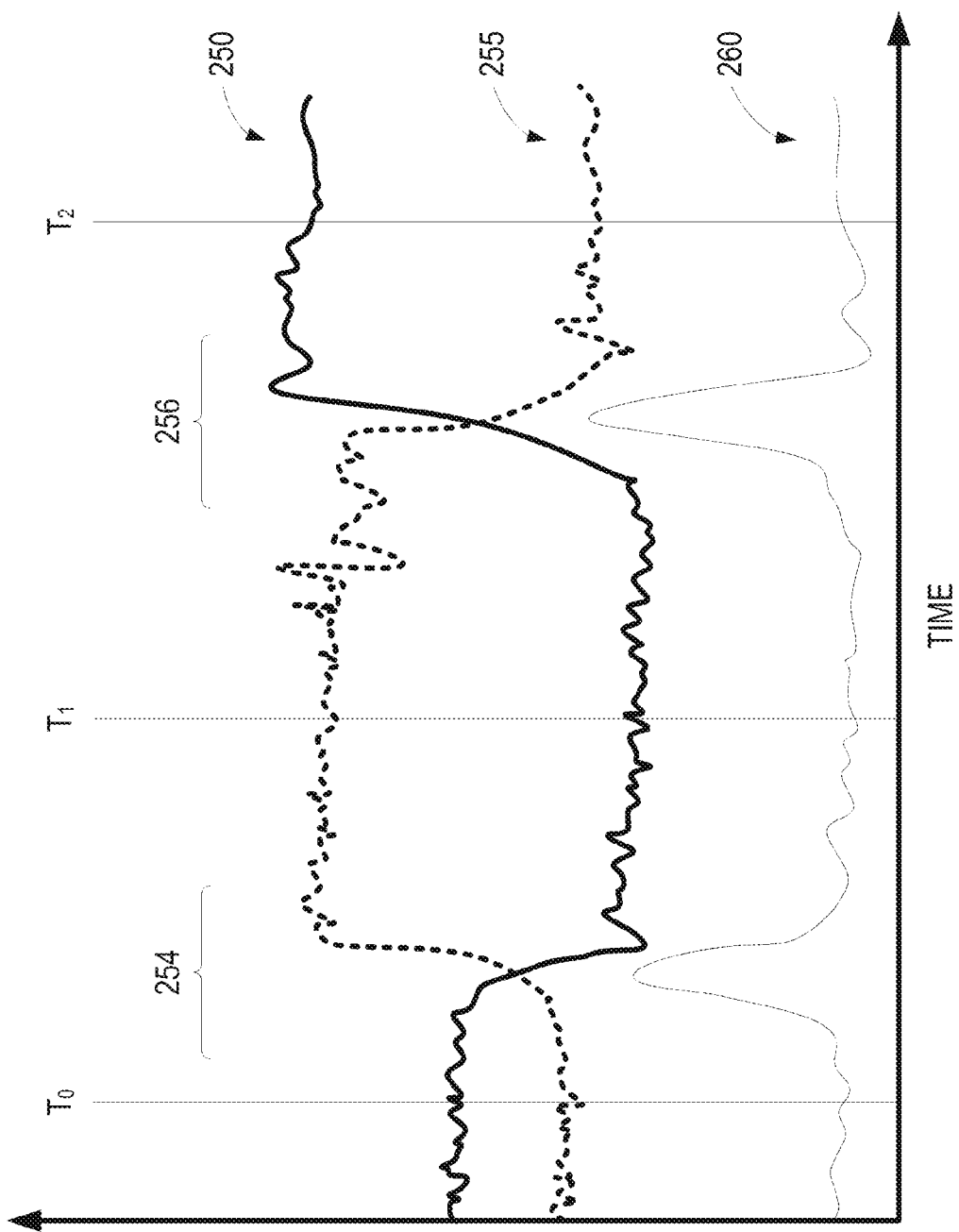
FIG. 2C is a graph illustrating data recorded with a wearable sensor.

FIG. 2C depicts a graph of data that may be obtained with the wearable sensor 200. As described above, in some implementations, the wearable sensor 200 detects orientation. The solid line 250 indicates the wearable sensor's orientation along a first axis and the dotted line 252 indicates the wearable sensor's orientation along a second axis. The method of determining if movement has occurred based on orientation is described in greater detail below. In general, the change in orientation is correlated with a movement of the wearable sensor 200. For example, in the time epochs 254 and 256 relatively large fluctuations are seen in both the orientation signals 250 and 252. In some implementations, the wearable sensor 200 (or other device described herein) quantifies movement to determine if the wearable sensor 200 is being worn during different epochs.

In some implementations, basing the detection of movement on orientation enables sampling at a relatively lower sampling rate when compared to basing the detection of movement on acceleration. The line 260 indicates an acceleration signal of the same wearable sensor 200. As illustrated, the acceleration signal is relatively steady except for during epochs of large movement. However, to capture the rapid change in accelerations, the sampling frequency must be high enough to accurately recreate the signal. For example, if a sample is only recoded at $t_0$, $t_1$, and $t_2$, (far below the Nyquist frequency of the acceleration signal 260)

then the acceleration signal would appear flat throughout the recording and it would appear as if no movement occurred. However, sampling at $t_0$, $t_1$, and $t_2$, provides data points with substantially different orientation values, and thus movement information may be determined from low sampled orientation data.

D. Power Efficient Measurement of Physical Activity with a Wearable Sensor

The systems and methods described herein relate to the power efficient measurement of physical activity with a wearable sensor. More particularly, the systems and methods described herein enable the continuous activity tracking without compromising battery life. In some implementations, the wearable sensor detects movement and enters predefined power states responsive to the type of movement detected.

While the invention has been particularly shown and described with reference to specific embodiments, it should be understood by those skilled in the art that various changes in form and detail may be made therein without departing from the spirit and scope of the invention described in this disclosure. For example, the methods described herein may be included in as a module that is added to an already available wearable sensor or custom built wearable sensor such as the wearable sensor described herein.

Figure 3:
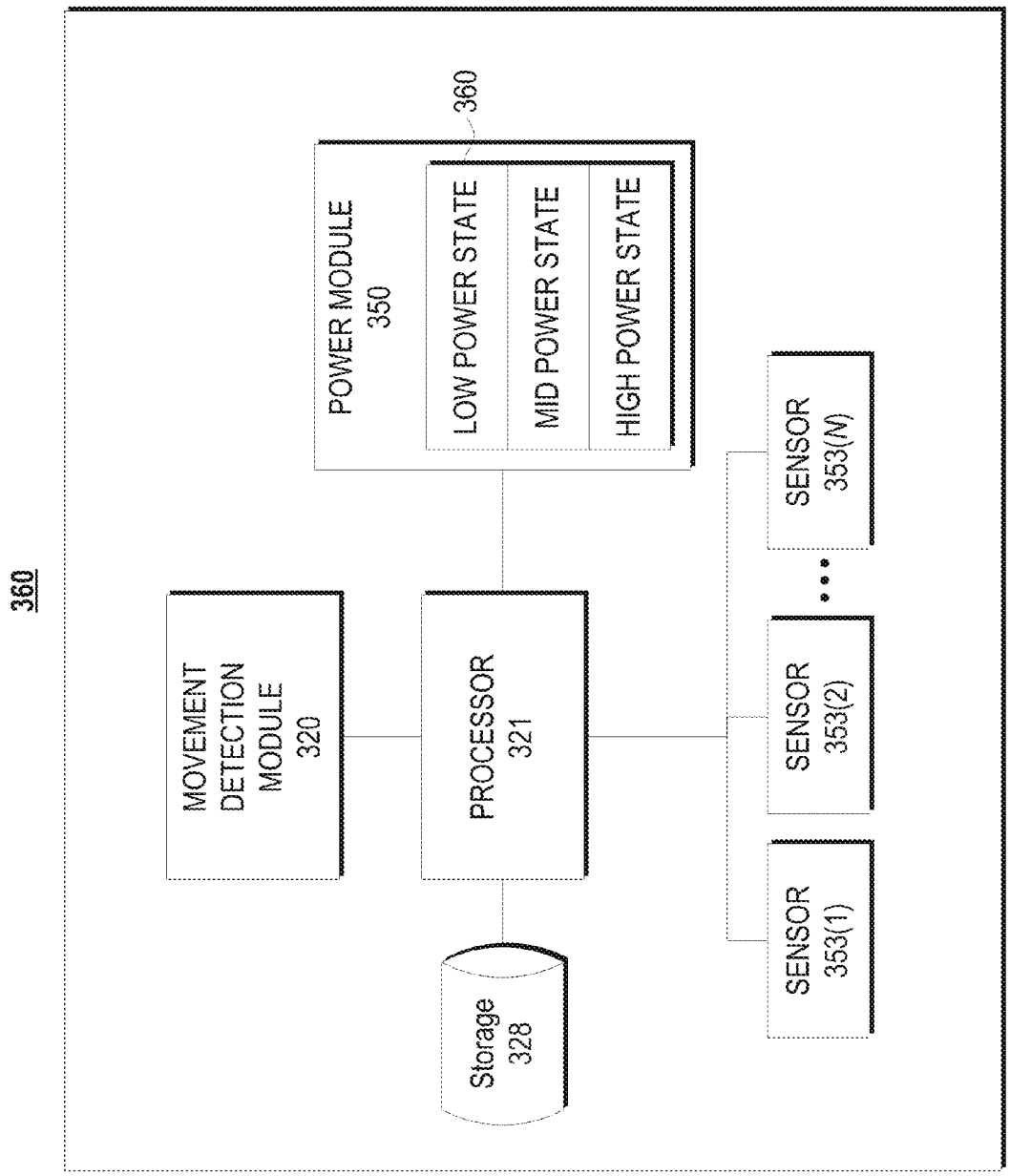
FIG. 3 is illustrates a block diagram of a schematic of an exemplary wearable sensor.

FIG. 3 depicts a schematic of an exemplary wearable sensor 300. In some implementations, the wearable sensor 300 is also referred to as a wearable device. The wearable sensor 300 is configured for the efficient measurement of physical activity. In addition to any of the components discussed above in relation to the wearable sensor 150 of FIG. 1A, the wearable sensor 300 includes a movement detection module 320, a power management module 350, a plurality of sensors 353(1)-353(N), a storage device 328, and a processor 321. The sensors 353 and the processor 321 can be similar to the components described above in relation to FIGS. 1A-1G.

As set forth above, the wearable sensor 300 can include a plurality of sensors 353. In some implementations, the wearable sensor 300 sets its power state responsive to a detection of movement or physical activity. The movement may be based on the wearable sensor's orientation and/or acceleration. The signal generated by the sensor 353 in response to detecting physical activity can be referred to as a motion signal. In some implementations, the orientation of the wearable sensor 300 is derived from the motion signal by measuring the gravitational acceleration along the x, y, and z axis. The accelerometers can be configured to detect subtle movements, such as those that are difficult to spot with the naked eye. For example, the sensor 353 may detect movements that are caused by a user breathing or chewing. In some implementations, the sensors can detect orientation to within 1 degree, 0.5 degrees, or 0.01 degrees. In addition to movement, and as described above, the wearable sensor 300 may detect medical conditions of the wearer such as, but not limited to, temperature, pulse rate, and blood pressure. In some implementations, the sensors 353 can include altimeter sensors and/or frequency modulation (FM) tuners.

In some implementations, the processor 321 samples the signal generated by the sensors 353 at less than 10 Hz. In some implementations, a sampling frequency less than 10 Hz is referred to as a low sampling frequency and a sampling frequency about 10 Hz is referred to as a high sampling frequency. The processor 321 can sample the signal at about 1-5 Hz, about 3-7 Hz, or about 6-10 Hz. In some implementations, the processor 321 samples the motion signal once per time step, wherein a time step can be 1 min, 5 min, or 10 min. In some implementations, the processor 321 samples the signal above 10 Hz. For example, the processor 321 can sample the signal at about 10-50 Hz, about 50-100 Hz, about 100-200 Hz, or about 200-1000 Hz.

The wearable sensor 300 also includes a movement detection module 320. The movement detection module 320 is responsible for detecting and determining when the wearable sensor 300 moves. The movement detection module 320 can be configured to detect and measure movements associated with physical activity (e.g., walking and exercising), sleep, and non-physical activity (e.g., sedentary activity or eating). In some implementations, the movements detection module 320 includes processor executable instructions that are stored in the storage device 328 or within the processor 321.

In some implementations, the detection module 320 detects movement or activity responsive to the orientation of the wearable sensor, as determined by one or more sensors 353. The orientation of the wearable sensor 300 at each sampled data point of the motion signal may be determined using the below equations:

$$\text{Pitch} = \arctan\left(\frac{G_y}{\sqrt{G_x^2 + G_z^2}}\right)$$

$$\text{Roll} = a c r \tan\left(\frac{-G_x}{G_z}\right)$$

In the above equations, $G_i$ represents the measured acceleration along the x, y, and z axes. In some implementations, the motion signal is filtered with a low pass filter to substantially isolate the acceleration due to gravity. The low pass filter can remove the component of the motion signal due to movement leaving substantially only the component caused by gravity.

In some implementations the measured acceleration may be used to determine both an orientation and an intensity. In some implementations, the intensity of the motion signal is the raw magnitude of the motion signal. In other implementations, intensity of the motion signal is a derived value that can be calculated from the raw motion signal. For example, the intensity value can be the sum of the absolute value of the differential of the samples in the motion signal. More particularly, the intensity can be represented by the equation:

$$I=\Sigma|x[n]-x[n+1]|$$

where I is the intensity of the motion signal and x[n] is the sampled motion signal at sample n.

In a similar implementations, the intensity value can be the sum of the absolute value of the samples in the motion signal and a running average. More particularly, the intensity can be represented by the equation:

$$I=\Sigma|x[n]-MA_x|$$

where I is the intensity of the motion signal and x[n] is the sampled motion signal at sample n. $MA_x$ is the moving average over the last x samples of the motion signal.

In some implementations, the movement detection module 320 determines if movement occurred responsive to an intensity or orientation crossing a threshold. For example, the movement detection module 320 may count the number of times the intensity rose above a first threshold within the time step. If the number is above a second threshold, the movement detection module 320 may inform the power management module 350 that movement occurred during the time step. In some implementations, a predetermined number of consecutive samples recorded during the time step have to cross the first threshold for the motion detection module 320 to indicate that a motion was detected.

Referring back to FIG. 3, the wearable sensor 300 also includes a power management module 350. In general, the power management module 350 automatically sets the wearable sensor's power state to one of the plurality of power states 360. As illustrated in FIG. 3, the power management module 350 includes a low power state, a mid-power state, and a high power state. In some implementations, each of the low power state, mid-power state, and high power state can have a plurality of sub states. For example, the low power state may include a default low power state and a deep low power state, which the power management module 350 enables if the movement detection module 320 has not detected movement in a predetermined amount of time.

In some implementations, as illustrated in FIG. 2C, movement data (e.g., wearable sensor orientation or acceleration) can include brief intervals of activity, surrounded by long segments of sedentary (or low) activity. As described in greater detail below, the power management module 350 can detect and classify movement and place the wearable sensor 300 in a lower power state during periods of substantially sedentary movement. The power management module 350 can also place the wearable sensor 300 in a high power state during periods of active movement. In some implementations, the mid power state is an intermediate state, during which time the power management module 350 determines if it should fully enter the high power state.

In some implementations, the power management module 350 classifies the movement data with a pattern recognition algorithm. The pattern recognition algorithm can be a decision tree classifier, artificial neural network, support vector machine, or Hidden Markov model. The classifiers may be trained through supervised or unsupervised learning. The classification by the algorithm can be responsive to the variance, entropy, frequency components, energy, or any combination thereof of the movement data. In some implementations, additional data such as a location or orientation may be used to classify the data.

In some implementations, the low power state is a sleep state. In the lower power state, the processor 321 can be set to a sleep or idle power state, wherein the wearable sensor may consume a negligent amount of energy. In some implementations, one or more of the sensors 353 are turned off or the processor 321 does not sample motion data from the sensors 353.

In some implementations, the mid-power state is also referred to the slope sense state. In the slope sense state, the movement detection module 320 monitors motion data captured via the sensors 353 to determine movement has (or is occurring). In some implementations, the movement must be above a predetermined threshold before the movement detection module 320 determines movement has occurred. For example, the movement detection module 320 may not indicate to the power management module 350 that movement was detected if the movement detection module 320 detects small movements, such as those occurring when a user of the wearable sensor breaths.

In some implementations, the wearable sensor 300 wakes form the low power state to the mid-power state at predetermined intervals. For example, the wearable sensor 300 may enter the slope sense state about every 5-60 seconds, 30-120 seconds, 1-3 minutes, 2-5 minutes, 5-10 minutes, or 10-30 minutes to determine if movement of the wearable sensor 300 is occurring. In some implementations, the wearable sensor 300 samples the motion signal once when waking from the low power state. For example, the wearable sensor 300 may sample the movement signal once every one minute to determine the wearable sensor's orientation. In another example, the wearable sensor 300 may sample the motion single for a predetermined length of time when waking from the low power state. For example, the wearable sensor 300 may sample the motion signal for 2 second every 1 minute to determine the intensity of the wearable sensor's movement. During the mid-power state the wearable sensor 300 may activate a subset of the plurality of sensors 353. In some implementations, if substantially no motion is detected the wearable sensor 300 may reenter the low power state.

In some implementations, during the high power state the processor 321 samples the motion signal at a higher relative frequency compared to the sampling frequency of the mid-power state. For example, the wearable sensor 300 may sample one or more motion signals at a about 10-20 Hz, 15-50 Hz, 40-100 Hz, or over 100 Hz. In some implementations, in the high power state, the wearable sensor 300 activates a greater number of sensors 353 relative to the number of sensors 353 activated in the mid-power state. In some implementations, the wearable sensor 300 enables all the sensors 353 within the wearable sensor 300.

Figure 4:
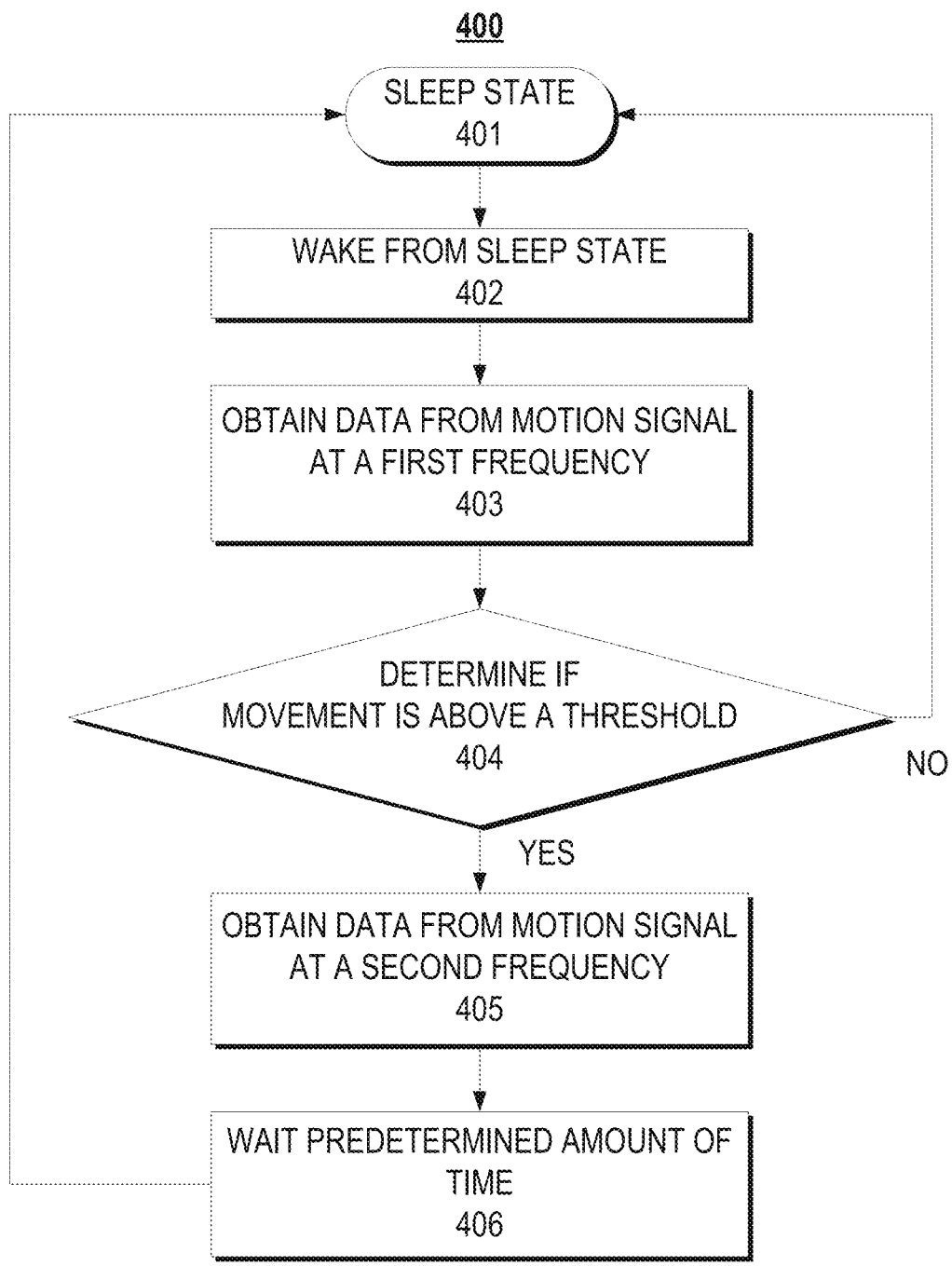
FIG. 4 is a flow chart of a method for measuring physical activity in a power efficient manner with a wearable sensor.

FIG. 4 depicts a flow chart of a method 400 for measuring physical activity in a power efficient manner with a wearable sensor. The method 400 begins with the wearable sensor in a sleep state (step 401). In some implementations, the sleep state is also referred to as a low power state. As described above, in the sleep state the components of the wearable sensor may consume a negligible amount of power. In some implementations, the processor of the wearable sensor enters a sleep state or standby mode when the wearable sensor is in the low power state. In some implementations, the method 400 is reiterated a plurality of times. Each iteration through the method 400 is termed a "step." The length of time that the wearable sensor is in the low power state is defined as $t_{sleep}$. In some, implementations $t_{sleep}$ is about 1-2 minutes, 2-5 minutes, or 5-10 minutes. As described below, in other implementations, the duration of $t_{sleep}$ is substantially optimized responsive a wearers sex, age, physical activity level, or height.

At step 402, the wearable sensor wakes from the sleep or low power state. In some implementations, at the expiration of $t_{sleep}$, a clock wakes the processor of the wearable sensor via an interrupt. In other implementations, the waking of the wearable sensor may occur responsive to a movement. For example, the wearable sensor may include a sensor coupled to an interrupt channel of the processor, such that the sensor can wake the processor (or wearable sensor) via the interrupt responsive to the detection of a movement.

At step 403, the wearable sensor obtains data from a motion signal at a first frequency. At step 403, the wearable sensor is in the above described mid-power (or slope sense) state. In some implementations, the wearable sensor measures the motion signal for a predetermined time $t_{slope}$. The duration of $t_{slope}$ can be about 0-2 seconds in duration. During the mid-power state, the wearable sensor may record a single sample from the motion signal. In some implementations, the wearable sensor samples the motion signal infrequently or at a low sampling frequency (e.g., less than 10 Hz). The wearable sensor may save the data recorded during the mid-power state to a storage device within the wearable sensor.

At step 404, the movement detection module of the wearable sensor determines if movement occurred during step 403. In some implementations, the movement detection module determines if the detected movement is above a predetermined threshold. In some implementations, the threshold is set to V. In some implementations, at least N samples recorded during the step 403 have to be above V for the movement detection module to determine that motion occurred during step 403.

In some implementations, the values of V and N are set responsive to the wearer of the wearable sensor. For example, the values V and N can be set responsive to a wearer's age, height, ethnicity, overall activity level, sex, health condition or any combination thereof. In some implementations, the values of V and N are calibrated response to motion signals (or other data) previously collected on the wearable sensor. In some implementations, the V and N parameters are set using an optimization algorithm that enables the wearer's physical activity to be characterized while substantially optimizing the power consumption of the wearable sensor. For example, a gradient descent algorithm may be used. In this example, the constraining variable can be the power consumption of the wearable sensor. In some implementations, the parameters are selected to reduce the least squared error between the an activity count over a period T and an activity count that is substantially less than T. In some implementations, the activity count can be the sum of the absolute values of the slopes of a motion signal. In some implementations, the activity count can calculated by integrating the motion signal. A penalty factor can be applied to the algorithm if the power consumption exceeds the set value.

In other implementations, the values of $t_{sleep}$, $t_{slope}$, V, and N are contestants. For example, $t_{sleep}$ may be about 30-60 seconds, 1-3 min, 3-5 min, or 5-10 min; $t_{slope}$ may be about 0-5 seconds, 5-25 seconds, 25-60 seconds.

As described above, in some implementations, at step 403, the wearable sensor records only one sample from the motion signal. The movement detection module may compare the orientation from the current time step or an orientation data point of a previous time step to determine if movement is occurring. If the difference between the present and past orientation samples is above a predetermined threshold, the movement detection module may determine that movement has occurred, and the wearable sensor may switch to a high power state.

At step 404, if the movement detection module of the wearable sensor does not detect movement, the wearable sensor may return to the sleep or low power state. In some implementations, the wearable sensor returns to the sleep or low power state after saving the data recorded during 403 to a storage device.

At step 405, responsive to detecting movement, the wearable sensor obtains data from the motion signal at a second frequency. The second frequency may be a frequency of 10 Hz or higher. The second frequency is higher than the first frequency used in step 403. At step 405, the power management module may enable the high power state. In some implementations, the wearable sensor may enable additional sensors or features of the processor. Measuring the motion signal at a relatively higher frequency may enable the wearable sensor to determine the orientation of the sensor and the intensity of the motion signal as described above.

The wearable sensor may obtain data at the second frequency for time $t_{record}$. In some implementations, $t_{record}$ is a predetermined amount of time. For example, the wearable sensor may record motion data for about 1-5 second, about 5-15 seconds, about 10-30 seconds, about 25-45 seconds, or about 40-60 second. In some implementations, $t_{record}$ is about 1-3 min, 3-5 min, or about 5-10 min. In some implementations, the wearable sensor resets $t_{record}$ if movement is detected when sampling at the second frequency.

In some implementations, the wearable sensor may also categorize the recorded motion signal along "cut points" (i.e., at changes in the characteristics of the motion signal). Example categories can include sedentary activity, light activity, moderate activity, vigorous activity, and sleeping. In some implementations, the wearable sensor can also identify specific activity such as going up or down stairs. In some implementations, the wearable sensor may also determine the amount of time that a wearer of the wearable sensor was in each category. For example, the wearable sensor may estimate the amount of time that the wearer sleeps each day. The wearable sensor may use additional information, such as location, to classify the recoded data. In some implementations, the categorization of the recorded data is performed on the wearable sensor. In other implementations, the categorization of the data occurs on a second device, such as a server. The categorization of the data can be automatic or performed by a human, such as a caretaker. As described above, the power management module of the wearable sensor may use decision trees, policies, artificial neural network, support vector machine, Hidden Markov model, Bayesian networks, clustering algorithms, or any combination thereof to categorize the data.

At step 406, the wearable sensor returns to the sleep state. In some implementations, the wearable sensor pauses for a predetermined amount of time prior to returning to a the sleep state. In some implementations, the wearable sensor may return to the mid-power state before fully returning to the sleep state.

What is claimed:

1. A method for efficiently measuring physical activity with a wearable device, the method comprising:
   waking a wearable device from a low power state, the wearable device comprising a motion sensor;
   obtaining, by the wearable device, one or more data points of a motion signal from the motion sensor at a first point in time with a first sampling frequency and;
   determining by the wearable device that the one or more data points are above a first threshold; and
   obtaining, by the wearable device, for a predetermined amount of time and at a second sampling frequency one or more additional data points of the motion signal responsive to the one or more data points being above the first threshold.

2. The method of claim 1, wherein obtaining the one or more data points further comprises:
   obtaining only one data point from the motion signal; and
   determining an orientation of the wearable device at the one data point.

3. The method of claim 1, wherein obtaining the one or more data points further comprises:
   obtaining a first data point from the motion signal;
   pausing for a second predetermined amount of time; and
   obtaining a second data point from the motion signal.

4. The method of claim 3, wherein determining that the one or more data points are above the first threshold further comprises determining that each of the first data point and the second data point are above the first threshold.

5. The method of claim 1, wherein determining that the one or more data points are above the first threshold further comprises:
   determining a number of data points in the one or more data points that are above the first threshold; and
   determining that the number is greater than a second threshold.

6. The method of claim 1, wherein determining that the one or more data points are above the first threshold further comprises determining that a consecutive subset of data points within the one or more data points are above the first threshold.

7. The method of claim 1, wherein determining that the one or more data points are above the first threshold further comprises determining that the absolute value of a difference between the one or more data points and a previous obtained data point is above the first threshold.

8. The method of claim 1, further comprising switching to the low power state at the end of the predetermined amount of time.

9. The method of claim 1, further comprising switching back to sampling the motion signal at the first sampling frequency at the end of the predetermined amount of time.

10. The method of claim 1, further comprising:
    comparing a subset of samples sampled at the second sampling frequency to a second threshold; and
    switching to the low power state that a predetermined number of the samples in the subset of samples are not greater than the second threshold.

11. The method of claim 1, wherein the second sampling frequency is greater than the first sampling frequency.

12. A wearable device comprising:
    a processor, coupled to a motion sensor, configured to:
    wake from a low power state;
    obtain one or more data points of a motion signal of the motion sensor at a first point in time at a first sampling frequency;
    determine that the one or more data points are above a first threshold; and
    obtain for a predetermined amount of time and at a second sampling frequency one or more additional data points of the motion signal responsive to the one or more data points being above the first threshold.

13. The wearable device of claim 12, wherein the processor is further configured to:
    obtain only one data point from the motion signal; and
    determine an orientation of the wearable device at the one data point.

14. The wearable device of claim 12, wherein the processor is further configured to:
    obtain a first data point from the motion signal;
    pause for a second predetermined amount of time; and
    obtain a second data point from the motion signal.

15. The wearable device of claim 13, wherein the processor is further configured to determine that the one or more data points are above the first threshold by determining that each of the first data point and the second data point are above the first threshold.

16. The wearable device of claim 12, wherein the processor is further configured to:
    determine a number of data points in the one or more data points that are above the first threshold; and
    determine that the number is greater than a second threshold.

17. The wearable device of claim 12, wherein the processor is further configured to determine that the one or more data points are above the first threshold by determining that a consecutive subset of data points within the one or more data points are above the first threshold.

18. The wearable device of claim 12, wherein the processor is further configured to switch to the low power state at the end of the predetermined amount of time.

19. The wearable device of claim 12, wherein the processor is further configured to switch back to sampling the motion signal at the first sampling frequency at the end of the predetermined amount of time.

20. The wearable device of claim 12, wherein the processor is further configured to:
    compare a subset of samples sampled at the second sampling frequency to a second threshold; and
    switch to the low power state that a predetermined number of the samples in the subset of samples are not greater than the second threshold.

21. The wearable device of claim 12, wherein the second sampling frequency is greater than the first sampling frequency.

* * * * *